(12) United States Patent
Dumesnil

(10) Patent No.: US 10,327,858 B2
(45) Date of Patent: Jun. 25, 2019

(54) WATER-RESISTANT VENTRICULAR ASSIST DEVICE BAG

(71) Applicant: Custom Design and Development, Inc., Katy, TX (US)

(72) Inventor: Curtis Dumesnil, Katy, TX (US)

(73) Assignee: CUSTOM DESIGN AND DEVELOPMENT, INC., Katy, TX (US)

( * ) Notice: Subject to any disclaimer, the term of this patent is extended or adjusted under 35 U.S.C. 154(b) by 157 days.

(21) Appl. No.: 15/453,184

(22) Filed: Mar. 8, 2017

(65) Prior Publication Data

US 2017/0258545 A1    Sep. 14, 2017

Related U.S. Application Data

(60) Provisional application No. 62/305,274, filed on Mar. 8, 2016, provisional application No. 62/305,285, filed on Mar. 8, 2016.

(51) Int. Cl.

| A61B 17/06 | (2006.01) |
|---|---|
| A61L 15/00 | (2006.01) |
| A61B 50/31 | (2016.01) |
| A61M 1/12 | (2006.01) |
| A61B 50/30 | (2016.01) |
| A61B 50/00 | (2016.01) |

(52) U.S. Cl.
CPC ............. *A61B 50/31* (2016.02); *A61M 1/122* (2014.02); *A61M 1/127* (2013.01); *A61B 2050/0088* (2016.02); *A61B 2050/3011* (2016.02); *A61B 2050/311* (2016.02); *A61B 2050/314* (2016.02); *A61M 2205/8206* (2013.01); *A61M 2205/8237* (2013.01); *A61M 2209/06* (2013.01)

(58) Field of Classification Search
CPC . A61B 50/31; A61B 50/312; A61B 2050/314; A61B 50/00; A61B 17/06114; A61B 17/06; A61M 1/122; A61M 1/1652; A61M 2209/06; A61F 2/0095; A61F 17/00; B65D 81/22; A45C 11/20
See application file for complete search history.

(56) References Cited

U.S. PATENT DOCUMENTS

| 3,289,822 A * | 12/1966 | Schumer ................ B65D 11/02 206/8 |
| 6,247,328 B1 * | 6/2001 | Mogil .................. A45C 7/0077 383/110 |

(Continued)

*Primary Examiner* — Rafael A Ortiz
(74) *Attorney, Agent, or Firm* — Bracewell LLP; Brad Y. Chin

(57) ABSTRACT

Embodiments provide a water-resistant VAD bag including an upper unit having the shape of a cylinder, a lower unit having the shape of a cylinder, a controller sleeve, a battery sleeve, two inserted sleeves positioned in between the controller sleeve and the battery sleeve, an inner sleeve, and an inner layer. The upper unit includes a first elongated strap with a clip and second elongated strap without a clip, a cover on top of the upper unit with a handle sewn into the cover, and a zipper around a bottom of the cover. The lower unit includes a connecting strap and a third elongated strap with a receptacle for the clip on the first elongated strap from the upper unit, where the zipper is on the top of the lower unit, and where the connecting strap and second elongated strap are sewn into the lower unit and the upper unit.

20 Claims, 11 Drawing Sheets

(56) References Cited

U.S. PATENT DOCUMENTS

| | | | |
|---|---|---|---|
| 7,153,025 B1* | 12/2006 | Jackson | A45C 7/0059 |
| | | | 383/2 |
| 8,807,412 B2* | 8/2014 | Thomas | A45C 11/00 |
| | | | 224/269 |
| 2005/0183446 A1* | 8/2005 | Fuchs | A45C 11/20 |
| | | | 62/457.7 |
| 2007/0084742 A1* | 4/2007 | Miller | A61B 17/3472 |
| | | | 206/438 |
| 2009/0057308 A1* | 3/2009 | Rothschild | A45F 4/06 |
| | | | 220/7 |
| 2010/0181220 A1* | 7/2010 | Dasara | A61B 50/31 |
| | | | 206/438 |
| 2017/0101249 A1* | 4/2017 | Hopkinson | A61B 50/00 |
| 2017/0239011 A1* | 8/2017 | Lucas | A61M 16/101 |

* cited by examiner

WATER-RESISTANT VENTRICULAR ASSIST DEVICE BAG

CROSS REFERENCE TO RELATED APPLICATION

This application is a non-provisional patent application claiming priority to and the benefit of U.S. Prov. Pat. Apps. Ser. No. 62/305,274 and Ser. No. 62/305,285, each filed Mar. 8, 2016, the entire disclosures of which are expressly incorporated herein by reference.

BACKGROUND

Field

Embodiments generally relate to a water-resistant bag for storing a medical electronic device. More specifically, embodiments relate to a water-resistant ventricular assist device (VAD) bag for carrying VAD devices, such as Heart-Ware® or HeartMate® devices, including, for example, HeartWare® or HeartMate® controllers and batteries, in showers or inclement weather conditions.

Description of the Related Art

Cardiac arrest and other cardiac health ailments are a major cause of death worldwide. Heart failure happens when the heart does not pump enough blood to meet the needs of a human body, causing fluid to build up in the lungs and body. Sometimes the heart becomes so weak that medicine cannot improve the symptoms. Often the only treatment option is a VAD.

VADs are mechanical pumps implanted into a human chest. VADs take over the pumping action of the area of the heart called the ventricle. VADs help a heart pump so that a person becomes stronger. A VAD system utilizes a centrifugal blood pump that is implanted into pericardial space for ventricular support. A percutaneous driveline connects the VAD mechanical pump to an external controller, which regulates the pump function and is powered by one or more batteries.

The use of VADs provides patient benefits in most conditions. The presence of water or moisture in contact with VADs is undesirable for many reasons. Water or moisture destroys electrical function of the VAD pumps and of the battery in a VAD system. Further, water or moisture partially or completely clogs components of the controller and is abrasive to components within the VAD pump. In addition, the constant or daily presence of water leaves rust on VAD system components, resulting in gradual wear and tear.

The restricted use of VADs in water environments or moisture conditions limits their benefits. VADs are not suitable for use in showers or in inclement weather. Plastic bags that cover VADs during showers or inclement weather are flimsy or do not provide adequate protection. Multiple plastic bags are oftentimes used to cover multiple components of the VAD system. Such plastic bags do not adequately seal compartments and components of the VAD system and do not properly position other lifestyle items. Further, plastic bag do not protect VAD devices from water and other debris that may stop the device from working while the wearer is in inclement weather.

Various kinds of backpacks or shoulder bags are available to protect a wearable component from water during various activities outside. These backpacks or shoulder bags are not designed for use with VAD devices and do not improve patient comfort and mobility while outside using the VAD device. Generally, bags are not custom designed for VADs and do not provide enough protection for the VAD, its controller, or batteries, while a patient is showering. Backpacks and shoulder bags can hold VAD devices, but are limited in restricting patient comfort and mobility while in the shower and using a VAD device. Such bags do not allow the user to quickly access the controls of a VAD system and replace the batteries. Such backpacks and shoulder bags are often bulky and do not have enough pockets to accommodate various VAD system components.

It is thus desirable to have a VAD bag that can quickly and easily be accessed and also one that provides water, moisture, and debris protection for the electronics contained in the bag itself while the user is in the shower or experiencing inclement weather. Further, it is desirable to have a VAD bag that allows the user to quickly access the controls and replace the batteries, and also one that provides protection for the electronics contained in the bag itself while the user is experiencing inclement weather. Accordingly, what is needed is a water-resistant bag for storing and protecting VAD devices, its controller, and batteries.

SUMMARY

Embodiments relate to a water-resistant VAD bag, a VAD system, and a method of making a water-resistant VAD bag for storing a VAD sensitive to water damage. More specifically, embodiments provide a water-resistant VAD bag including an upper unit of flexible nylon having the shape of a cylinder, a lower unit of flexible nylon having the shape of a cylinder, a controller sleeve, a battery sleeve, two inserted sleeves positioned in between the controller sleeve and the battery sleeve, an inner sleeve, and an inner layer. The upper unit includes a first elongated strap with a clip on a first end and second elongated strap on a second end without a clip, a cover on top of the upper unit with a handle sewn into the cover, and a zipper around a bottom of the cover. The lower unit includes a connecting strap and a third elongated strap with a receptacle for the clip on the first elongated strap from the upper unit, where the zipper is on the top of the lower unit, and where the connecting strap and second elongated strap are sewn into the lower unit and the upper unit. The controller sleeve is insertable into the lower unit of the water-resistant VAD bag and includes a controller compartment for housing a VAD controller sensitive to water damage. The battery sleeve is insertable into the lower unit of the water-resistant VAD bag and includes at least one battery compartment for housing at least one VAD battery sensitive to water damage. The inner sleeve is insertable into the lower unit of the water-resistant VAD bag, has the shape of a circle, and covers the controller sleeve and the battery sleeve. The inner layer is insertable into the lower unit of the water-resistant VAD bag and positioned inside the lower unit.

According to at least one embodiment, the water-resistant VAD bag further includes a controller sleeve configured to block entry of moisture into the controller compartment. In some embodiments, the battery sleeve is configured to block entry of moisture into the battery compartment. According to one embodiment, the controller compartment is about 4.5 inches in height and about 21 inches in circumference. The battery compartment is substantially of cubic shape with dimensions of about 2.25 inches by about 4.25 inches by about 3.25 inches. The upper unit has a circumference of about 21.25 inches and the lower unit has a circumference of about 24.25 inches. The upper unit has a height measured from the zipper to the handle of about 3.25 inches or about 4.25 inch or about 1 inch. The total height of the combination of the upper unit and the lower unit measured from the handle to the bottom of the lower unit is about 6.75 inches or is about 9 inches. Webbing circumscribes the upper unit and is about 1 inch thick. The clip is about 0.75 inch long. The top of the handle is a rectangle of about 4.25 inches by about 1.5 inches or a rectangle of about 3.75 inches by about 1.25 inches. In some embodiments, the top of the handle is a rectangle of about 4.25 inches by about 1.5 inches or a rectangle of about 3.75 inches by about 1.25 inches. The two inserted sleeves are separated by a distance of about 1.75 inches. The inserted sleeve is substantially a rectangle of about 4.25 inches by about 7.25 inches. The inserted sleeve and inner sleeve are separated by a distance of about 0.75 inch.

According to another embodiment, there is provided a water-resistant VAD system including a water-resistant percutaneous lead for electrically coupling the VAD controller to a VAD pump and for regulating VAD pump function and an AC adapter for electrically coupling the VAD controller to an electrical outlet. In some embodiments, the water-resistant VAD further includes a power module for providing continuous power to the VAD system, a battery charger for providing external battery power to the VAD controller, or an external display device for presenting performance.

According to another embodiment, there is provided a method of making a water-resistant VAD bag sensitive to water damage including providing the upper unit, providing the lower unit, positioning at least one inserted sleeve in between a controller sleeve and a battery sleeve, providing an inner sleeve into the lower unit of the water-resistant VAD bag to cover the controller sleeve and the battery sleeve, providing the inner layer into the lower unit of the water-resistant VAD bag to cover the lower unit, sealing the upper unit with the lower unit by zipping the zipper around a bottom of the upper unit and the top of the lower unit, and clipping the upper unit with the lower unit by engaging a clip on a first end with a receptacle for the clip on a third elongated strap.

BRIEF DESCRIPTION OF DRAWINGS

These and other features, aspects, and advantages of the invention are better understood with regard to the following Detailed Description, Claims, and accompanying Figures. It is to be noted, however, that the Figures illustrate only various embodiments of the disclosure and are therefore not to be considered limiting of the invention's scope as it can admit to other equally effective embodiments.

DETAILED DESCRIPTION

Figure 1:
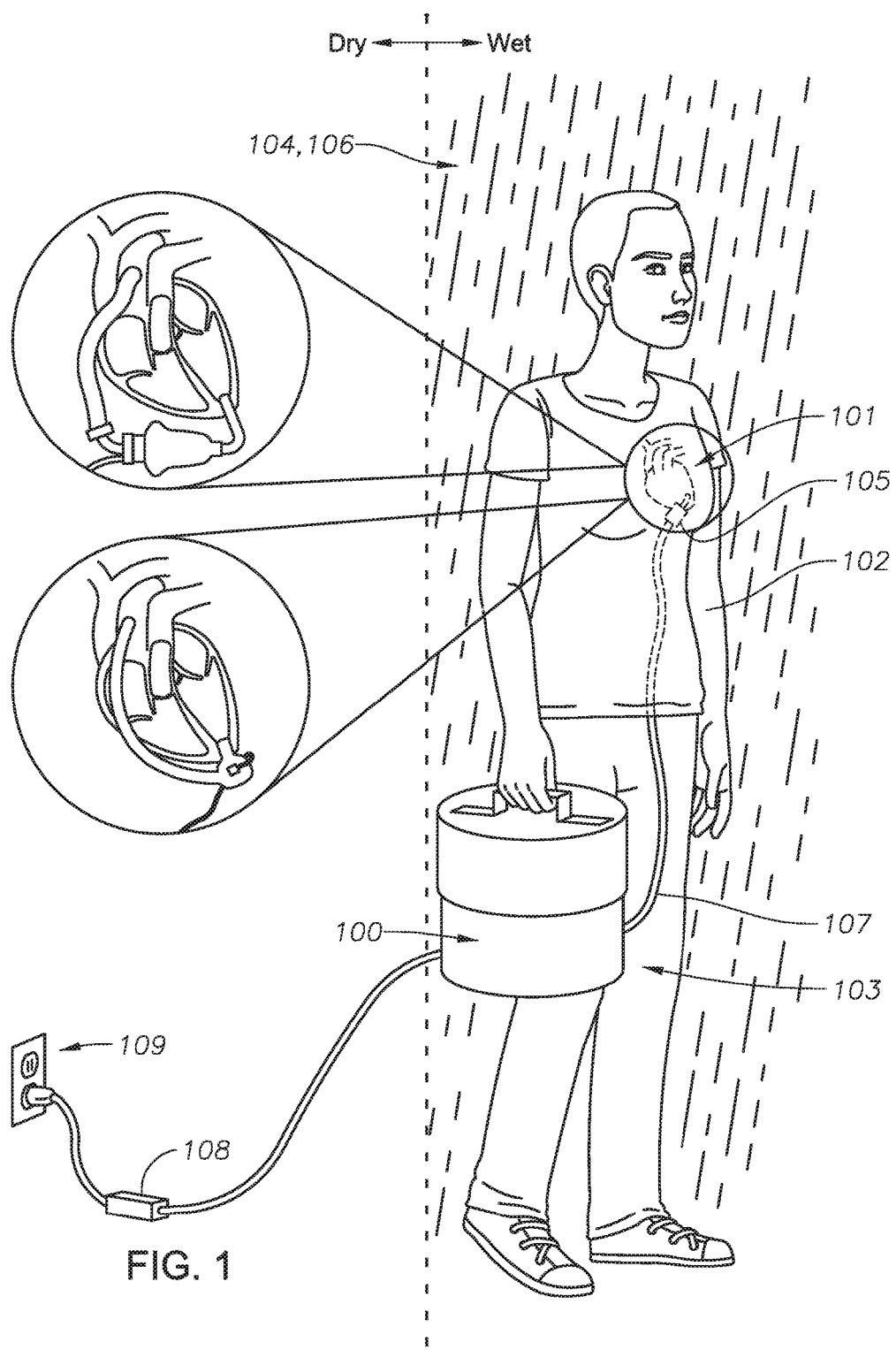
FIG. 1 is a full view of the water-resistant VAD bag for use in a shower or in inclement weather.

The foregoing aspects, features, and advantages of the present technology will be further appreciated when considered with reference to the following description of preferred embodiments and accompanying drawings, wherein like reference numerals represent like elements. The following is directed to various exemplary embodiments of the disclosure. The embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment. Like numbers refer to like elements throughout. In an embodiment, usage of the term "about" includes +/−5% of the cited magnitude. In an embodiment, usage of the term "substantially" includes +/−5% of the cited magnitude.

For simplicity and clarity of illustration, the drawing figures illustrate the general manner of construction, and descriptions and details of well-known features and techniques may be omitted to avoid unnecessarily obscuring the discussion of the described embodiments of the invention. Additionally, elements in the drawing figures are not necessarily drawn to scale. For example, the dimensions of some of the elements in the figures may be exaggerated relative to other elements to help improve understanding of the various embodiments. Like reference numerals refer to like elements throughout the specification. Hereinafter, various embodiments will be described in detail with reference to the accompanying drawings.

FIG. 1 is a full view of the water-resistant VAD bag 100 for use in a shower 104 or in inclement weather 106 by a patient 102. A VAD system 103, which may include a VAD pump 105, a water-resistant percutaneous lead 107, an AC adapter 108 that is plugged into an electrical outlet 109, a VAD bag 100, a VAD controller 152 (shown in FIG. 4C), and one or more VAD batteries 162 (shown in FIG. 4D), may be used to maintain blood to the patient 102, while in a wet environment. Thus, for example, the function of the VAD system 103 is maintained while the patient 102 partakes in daily activities that may involve exposure to water, moisture, or debris in the external environment. In some embodiments, the AC adapter 108 and the electrical outlet 109 are positioned outside of the shower 104 or inclement weather 106 to prevent water or moisture contact, yet the water-resistant VAD bag 100 is held by patient 102 inside of the shower 104 or inclement weather 106. Thus, for example, the percutaneous lead 107 and water-resistant VAD bag 100 protect internal electrical components from the water in any wet environment, while the AC adapter 108 and the electrical outlet 109 remain in a dry environment.

As further shown in FIG. 1, the water-resistant percutaneous lead 107, which electrically couples the VAD controller (shown in FIG. 4C) to a VAD pump 105 and which regulates VAD pump 105 function, may be waterproof or covered with a water-resistant material. The VAD pump 105, which may be, for example, a centrifugal blood pump that is implanted into a pericardial space for ventricular support, is located inside of the patient 102 and is not exposed to water. The AC adapter 108, which may be waterproof or covered with a water-resistant material, electrically couples the VAD controller 152 to the electrical outlet 109. In some embodiments, for example, the VAD bag 100, when coupled together with the water-resistant percutaneous lead 107, the VAD pump 105, and the AC adapter 108, provides water resistance to an entire VAD system 103 for use in the shower 104 or in inclement weather 106. Thus, for example, a patient 102 can comfortably shower or remain mobile, while still utilizing the exemplary VAD system 103 according to various embodiments.

As further shown in FIG. 1, in the closeup of the heart region 101, the VAD pump 105 may be, for example, a HeartMate® II Blood Pump or a Heartware® Blood Pump. In certain embodiments, a pacemaker or a Heartware® monitor may take the place of the VAD pump 105. The Heartware® VAD 105, which may be a new generation HVAD centrifugal flow VAD, is smaller device than the HeartMate® II VAD pump 105. In some embodiments, the larger HeartMate® II device requires a VAD controller 152 (shown in FIG. 4C) and a VAD battery 162 (shown in FIG. 4D) that are taller than the equivalent components in a Heartware® VAD pump 105. According to at least one embodiment, the water-resistant VAD bag 100 utilized for the HeartMate® II Blood Pump or a Heartware® Blood Pump will differ in dimensions (as shown in FIGS. 2E and 3F). The VAD pump 105 may be implanted alongside a patient's 102 heart's left ventricle or may be placed just below the diaphragm in the abdomen. The VAD pump 105 may be attached to the aorta and leave natural circulation in place, while providing all of the energy necessary to propel blood throughout the patient's 102 body. In certain embodiments, the VAD pump 105 may pump up to 10 liters of blood per minute covering the full output of a healthy heart, and provide long-term cardiac support for patients who have advanced-stage heart failure. In some embodiments, the VAD pump 105 is about 55 cubic centimeters and about 160 grams and includes an impeller that is suspended through a combination of passive magnetic and hydrodynamic forces.

Figure 2A:
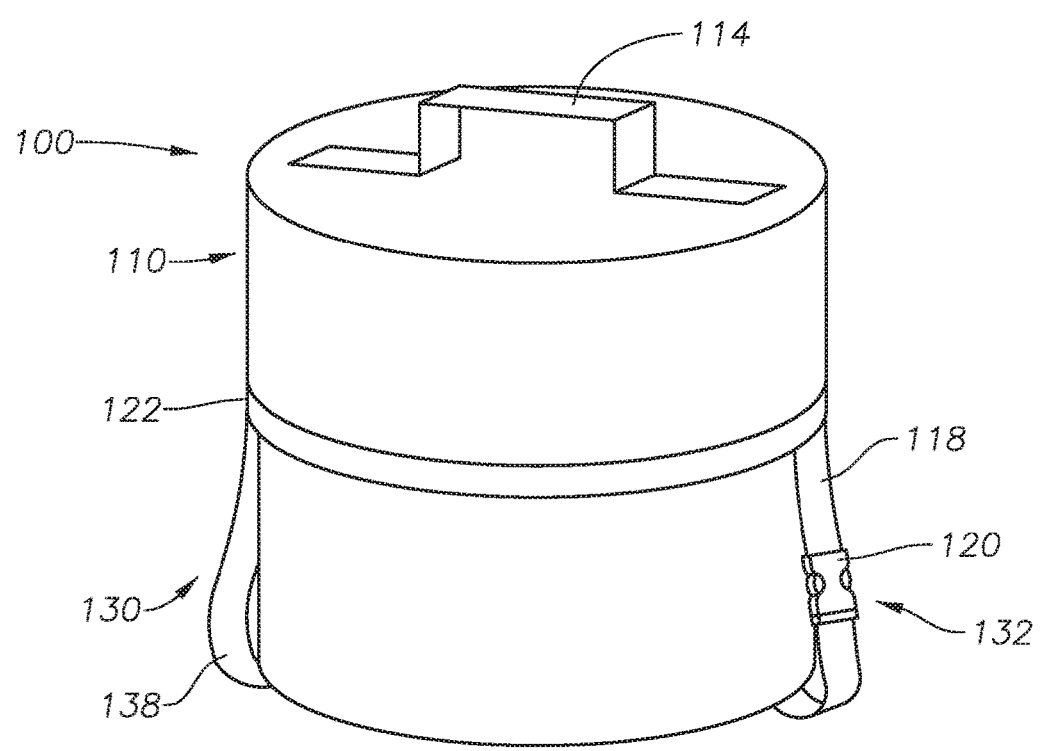
FIG. 2A is a side view of the entire water-resistant VAD bag according to an embodiment.

FIG. 2A is a side view of the entire water-resistant VAD bag 100 according to an embodiment. According to at least one embodiment, the water-resistant VAD bag 100 includes an upper unit 110 of flexible nylon having the shape of a cylinder, a lower unit 130 of flexible nylon having the shape of a cylinder, a controller sleeve 154 (shown in FIG. 4C), a battery sleeve 164 (shown in FIG. 4D), two inserted sleeves (which may be a first inserted sleeve 156 and a second inserted sleeve 158, as shown in FIG. 4E) positioned in between the controller sleeve 154 and the battery sleeve 164, an inner sleeve 146, and an inner layer 148. The lower unit 130 of the water-resistant VAD bag 100 includes a connecting strap 138 and a third elongated strap 134 with a receptacle 132 for the clip 120 on the first elongated strap 118 from the upper unit 110.

Figure 2B:
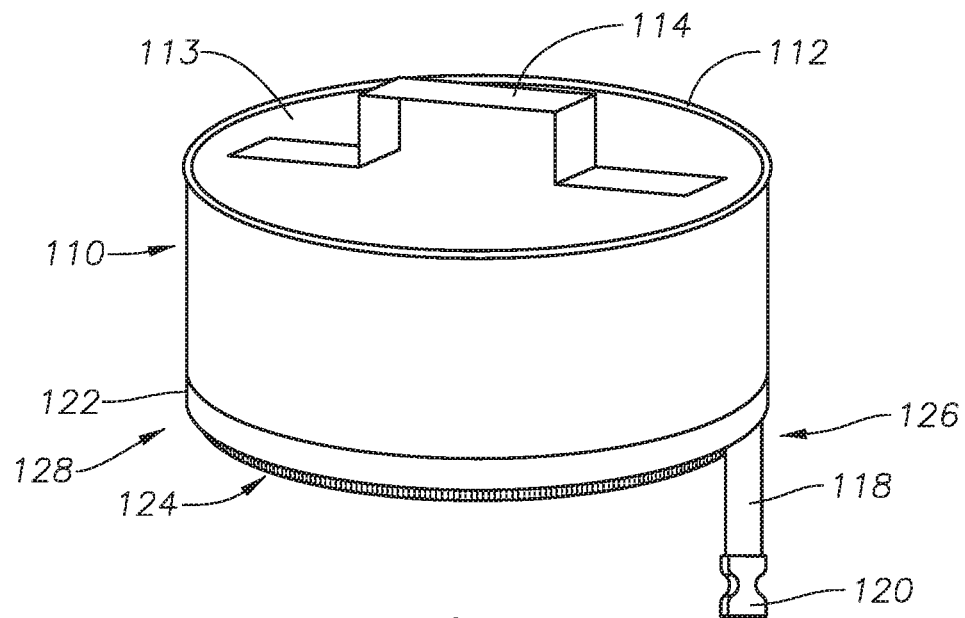
FIG. 2B is a view of the upper unit of the water-resistant VAD bag according to an embodiment.

FIG. 2B is a view of the upper unit 110 of the water-resistant VAD bag 100 according to an embodiment. The upper unit 110 includes a first elongated strap 118 with a clip 120 on a first end 126 and second elongated strap 122 on a second end 128 without a clip, a cover 113 on top of the upper unit 110 with a handle 114 sewn into the cover 113, and a zipper 124 around a bottom of the upper unit 110. In certain embodiments, there may be 12 stitches per inch in the upper unit and the zipper 124 may be a #8 zipper chain that is 23 inches. The cover 113 may be attached to a handle 114 and pipping 112 that surrounds the circumferential edge of the cover 113.

Figure 2C:
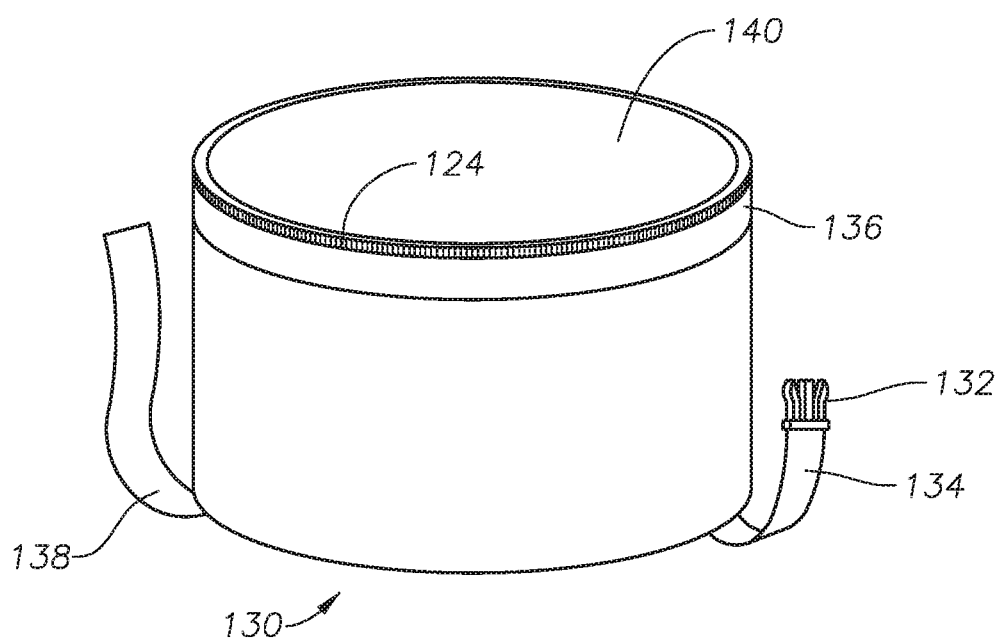
FIG. 2C is a view of the lower unit of the water-resistant VAD bag according to an embodiment.

FIG. 2C is a view of the lower unit 130 of the water-resistant VAD bag 100 according to an embodiment. A lid 140 can seal the VAD controller 152 (shown in FIG. 4C) and the VAD battery 162 (shown in FIG. 4D) inside of the water-resistant VAD bag 100 according to an embodiment. The lid 140 is placed on top of the lower unit 130 to protect the VAD controller 152 (shown in FIG. 4C) and the VAD battery 162 (shown in FIG. 4D) from water, moisture, and debris. In some embodiments, each of the connecting strap 138, third elongated strap 134, and zipper 124 may be sewn into the lower unit 130. A receptacle 132 may be coupled to the third elongated strap 134. A webbing 136, which may be 1 inch thick, may be attached to or sewn into the lower unit 130 and may cover the zipper 124 after it is zipped to the upper unit 110.

By assembling together the upper unit 110 of FIG. 2B and the lower unit 130 of FIG. 2C, the lower unit 130 becomes connected with the upper unit 110 through the use of the zipper 124, which is on the top of the lower unit 130. Thus, for example, by zipping the zipper 124, the lower unit 130 and the upper unit 110 combine to form one combined water-resistant VAD bag 100. The lower unit 130 and the upper unit 110 are optionally secured by the connecting strap 138 sewn into the lower unit 130 and sewn into the upper unit 110. In some embodiments, the lower unit 130 and upper unit 110 are also optionally secured by the second elongated strap 122 sewn into the lower unit 130 and sewn into the upper unit 110. In certain embodiments, the lower unit 130 is also optionally coupled to the upper unit 110, when clipping the clip 120 into a receptacle 132, and additionally because of the connecting strap 138 sewn into the lower unit 130 and sewn into the upper unit 110. Thus, for example, the water-resistant VAD bag 100 provides for multiple and redundant mechanisms to secure the lower unit 130 together with the upper unit 110, such as through use of the second elongated strap 122, the clip 120, and/or connecting strap 138.

In some embodiments, the lower unit 130 and the upper unit 110 may be assembled together to form the water-resistant VAD bag 100. In certain embodiments, the method of making the water-resistant VAD bag 100 for storing a VAD system 103 sensitive to water includes providing the upper unit 110, providing the lower unit 130, positioning at least one inserted sleeve (either or both first inserted sleeve 156 or second inserted sleeve 158) in between the controller sleeve 154 (shown in FIG. 4C) and the battery sleeve 164 (shown in FIG. 4D), providing the inner sleeve 148 (shown in FIGS. 4A and 4B) into the lower unit of the VAD bag to cover the controller sleeve 154 (shown in FIG. 4C) and the battery sleeve 164 (shown in FIG. 4D), providing the inner layer 148 into the lower unit 130 of the water-resistant VAD bag 100 to cover the lower unit 130, sealing the upper unit 110 with the lower unit 130 by zipping the zipper 124 around a bottom of the lid 140 and the on the top of the lower unit 130, and clipping the upper unit 110 with the lower unit 130 by engaging the clip 120 on the first end 126 with the receptacle 132 for the clip 120 on the third elongated strap 134. In certain embodiments, the entire water-resistant VAD bag 100 may be assembled and sewn together from six pieces of cloth.

Figure 2D:
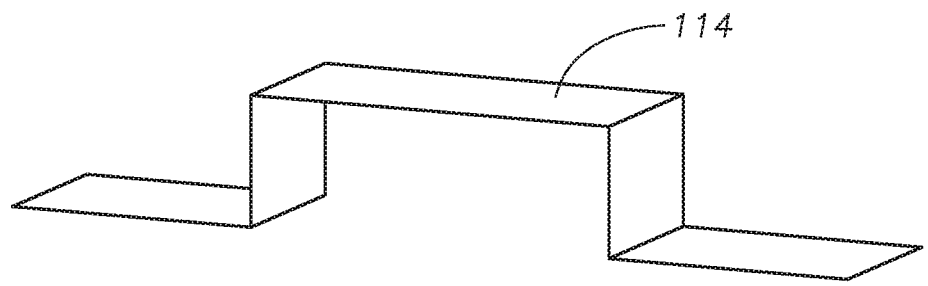
FIG. 2D is a view of the handle attached to the water-resistant VAD bag according to an embodiment.
Figure 2E:
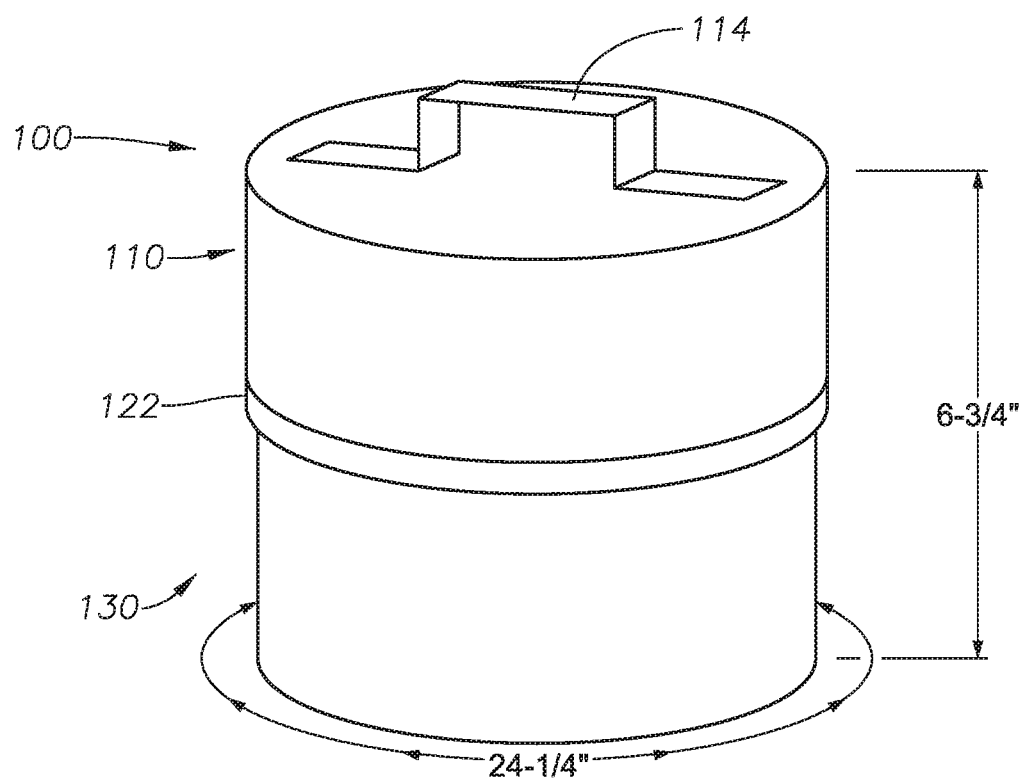
FIG. 2E is a view of the entire water-resistant VAD bag employing a HeartWare® device according to a dimensioned embodiment.

FIG. 2D is a view of the handle 114 attached to the water-resistant VAD bag 100 according to an embodiment. The handle 114 may be durable and detachable and can connect with connector clips (not shown) with the top of the water-resistant VAD bag 100.

FIG. 2E is a view of the entire water-resistant VAD bag 100 employing a HeartWare® device as the VAD pump 105 according to a dimensioned embodiment. In certain embodiments, a water-resistant VAD bag 100 employing a Heart-Ware® device has an lower unit 130 with a circumference of about 24.25 inches, and the combination of the upper unit 110 and the lower unit 130 measured from the handle 114 to the bottom of the lower unit 130 is about 6.75 inches or is about 9 inches.

Figure 2F:
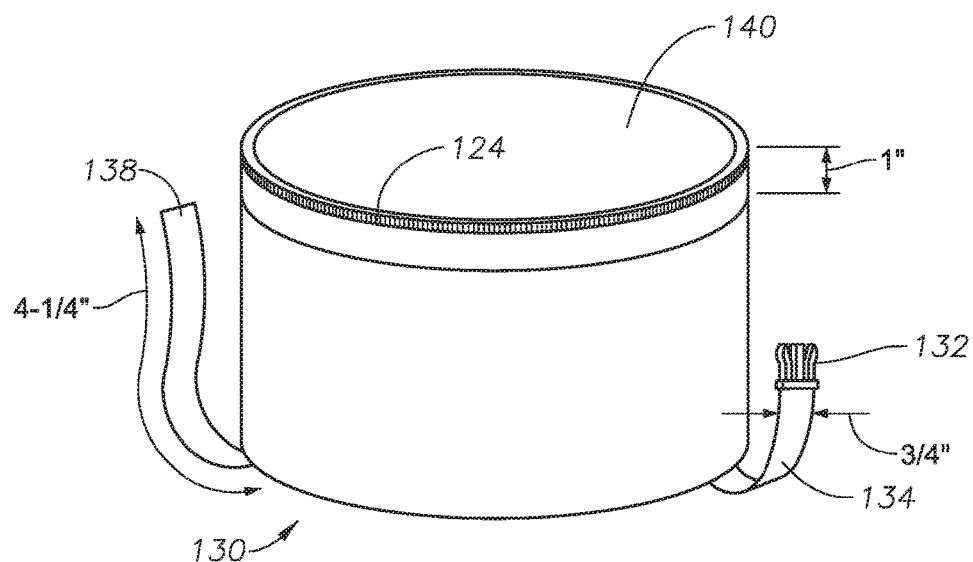
FIG. 2F is a view of the lower unit of the water-resistant VAD bag employing a HeartWare® device according to a dimensioned embodiment.

FIG. 2F is a view of the lower unit 130 of the water-resistant VAD bag 100 employing a HeartWare® device as the VAD pump 105 according to a dimensioned embodiment. In certain embodiments, the connecting strap 138 is about 4.25 inches long and the clip is about 0.75 inch long in conjunction with the use of a HeartWare® device as the VAD pump 105.

Figure 2G:
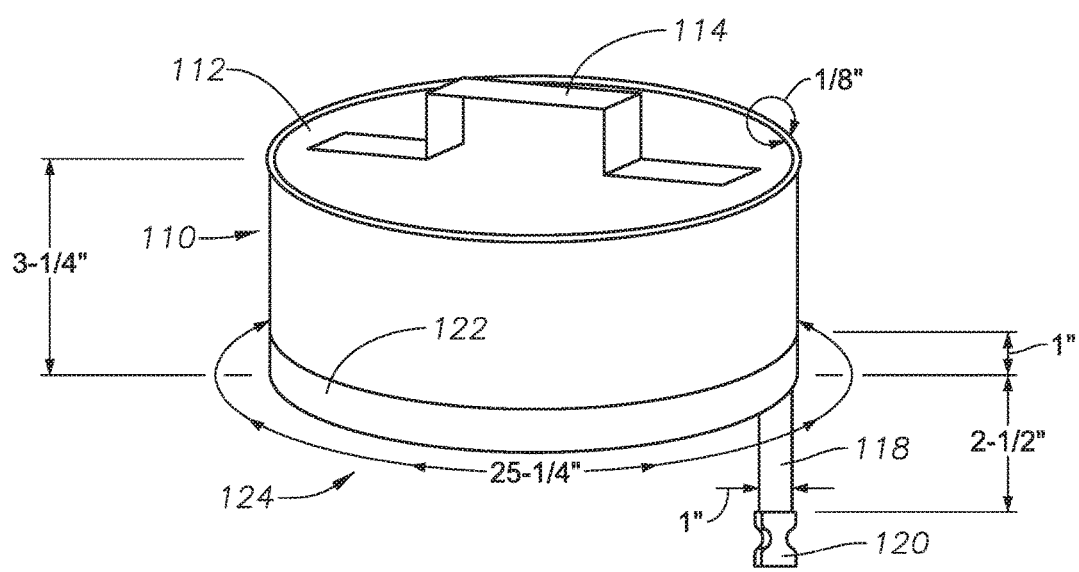
FIG. 2G is a view of the upper unit of the water-resistant VAD bag employing a HeartWare® device according to a dimensioned embodiment.

FIG. 2G is a view of the upper unit 110 of the water-resistant VAD bag 100 employing a HeartWare® device according to a dimensioned embodiment. In certain embodiments, the first elongated strap 118 is about 1 inch thick and about 2.5 inches long and the second elongated strap 122 is about 1 inch thick. In some embodiments, the upper surface of the upper unit 110 has a pipping 112 of ⅛ inch thickness surrounding the circumference of the upper unit 110. In certain embodiments, the upper unit is 3.25 inches in height and with a circumference measuring 25.25 inch. In some embodiments, the second elongated strap 122 covers the zipper 14 to protect the zipper from water, moisture, or debris from the external environment.

Figure 2H:
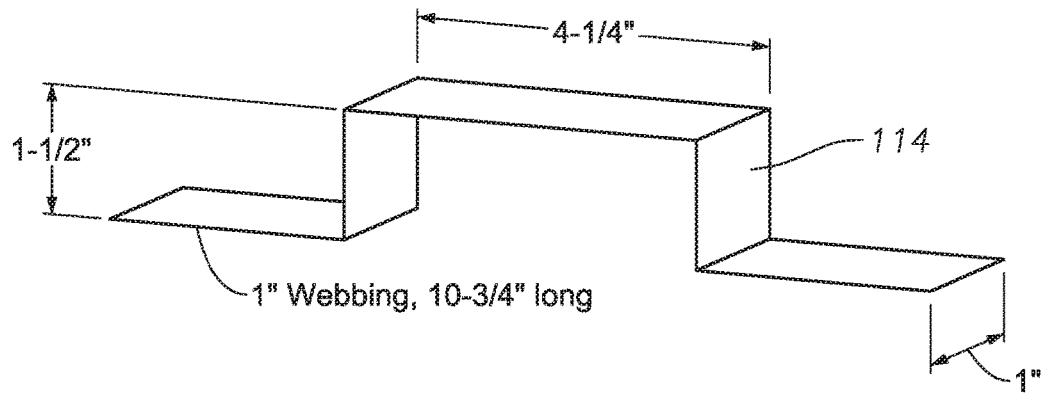
FIG. 2H is a view of the handle attached to the water-resistant VAD bag employing a HeartWare® device according to a dimensioned embodiment.

FIG. 2H is a view of the handle 114 attached to the water-resistant VAD bag 100 employing a HeartWare® device according to a dimensioned embodiment. In certain embodiments, the top of the handle 114 is a rectangle of about 4.25 inches by about 1.5 inches or a rectangle of about 3.75 inches by about 1.25 inches.

Figure 3A:
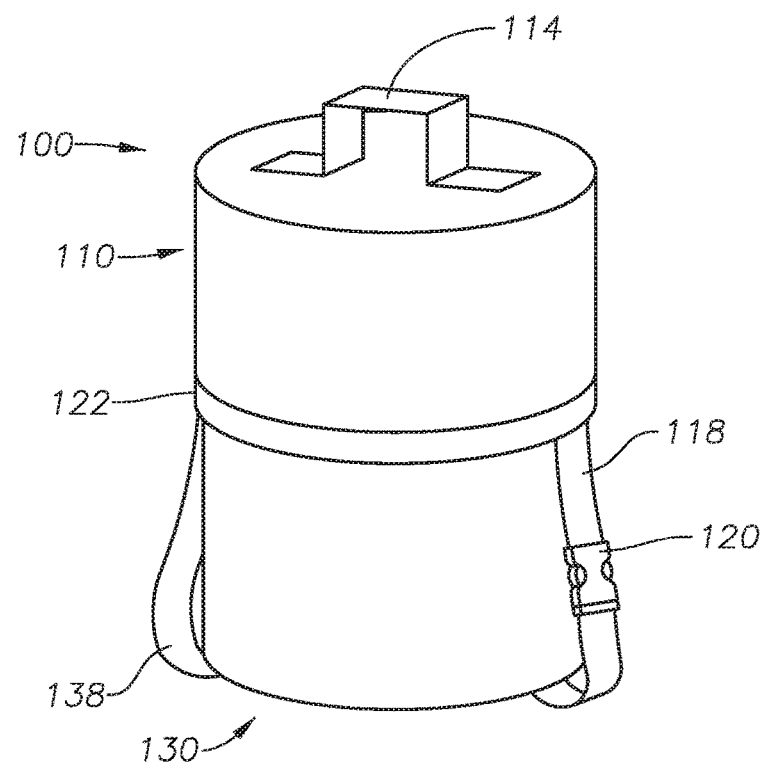
FIG. 3A is a view of the entire water-resistant VAD bag employing a HeartMate® device according to an embodiment.
Figure 3B:
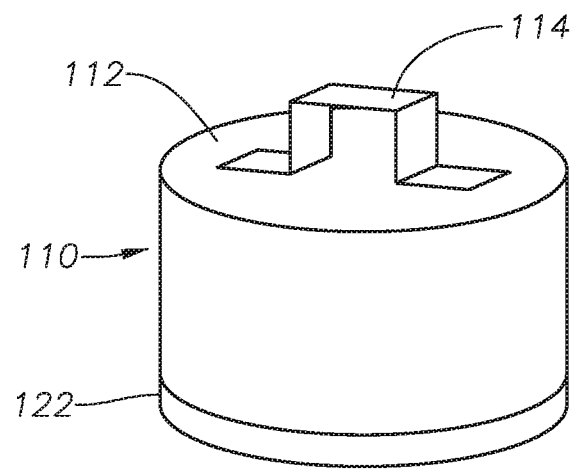
FIG. 3B is a view of the upper unit of the water-resistant VAD bag employing a HeartMate® device according to an embodiment.
Figure 3C:
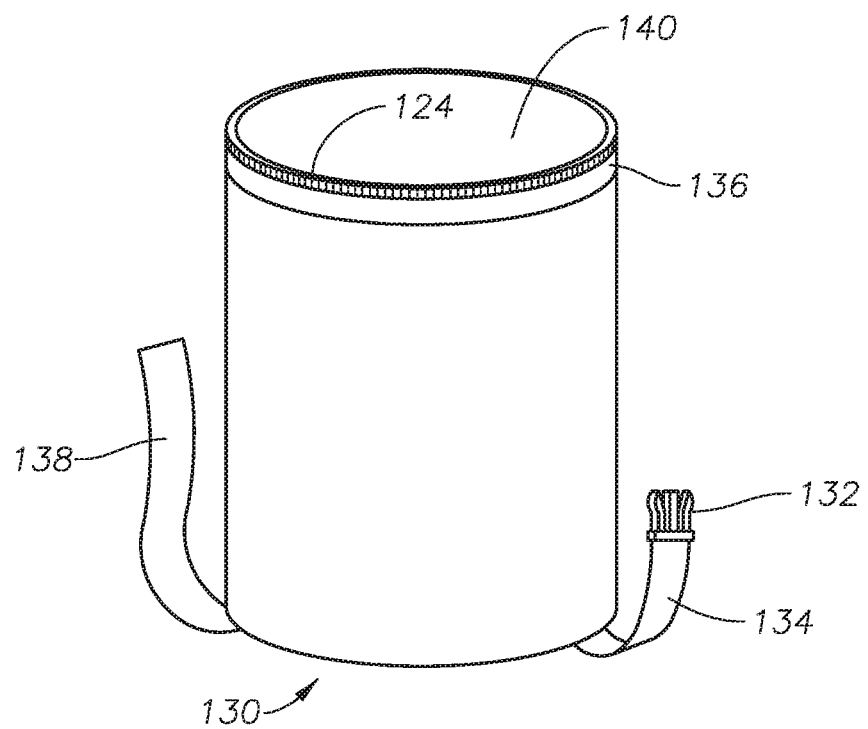
FIG. 3C is a view of the lower unit of the water-resistant VAD bag employing a HeartMate® device according to an embodiment.
Figure 3D:
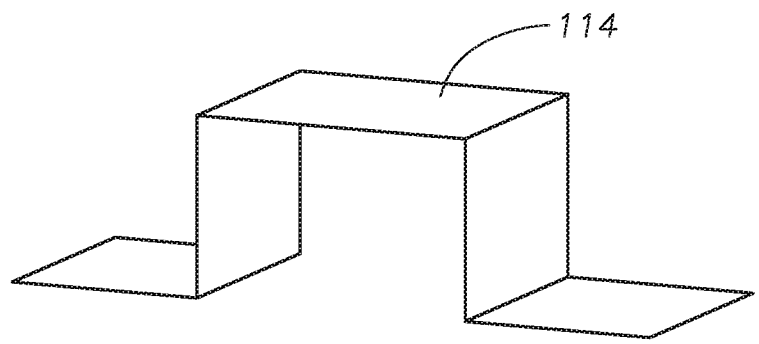
FIG. 3D is a view of the handle attached to the water-resistant VAD bag employing a HeartMate® device according to a dimensioned embodiment.
Figure 3E:
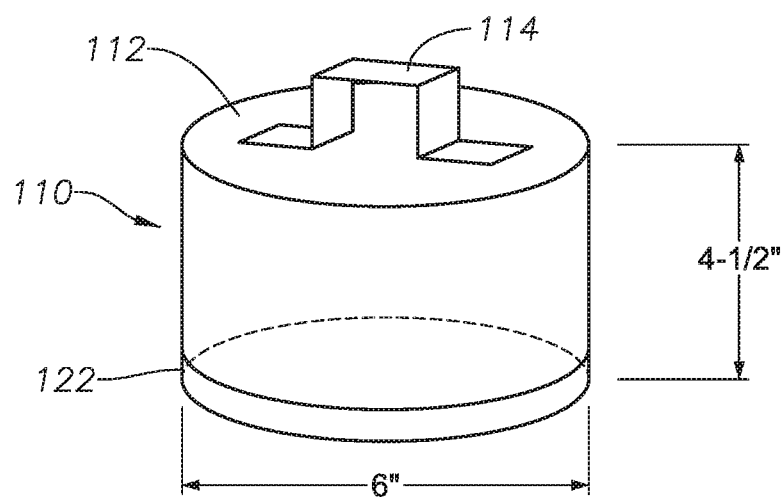
FIG. 3E is a view of the upper unit of the water-resistant VAD bag employing a HeartMate® device according to a dimensioned embodiment.
Figure 3F:
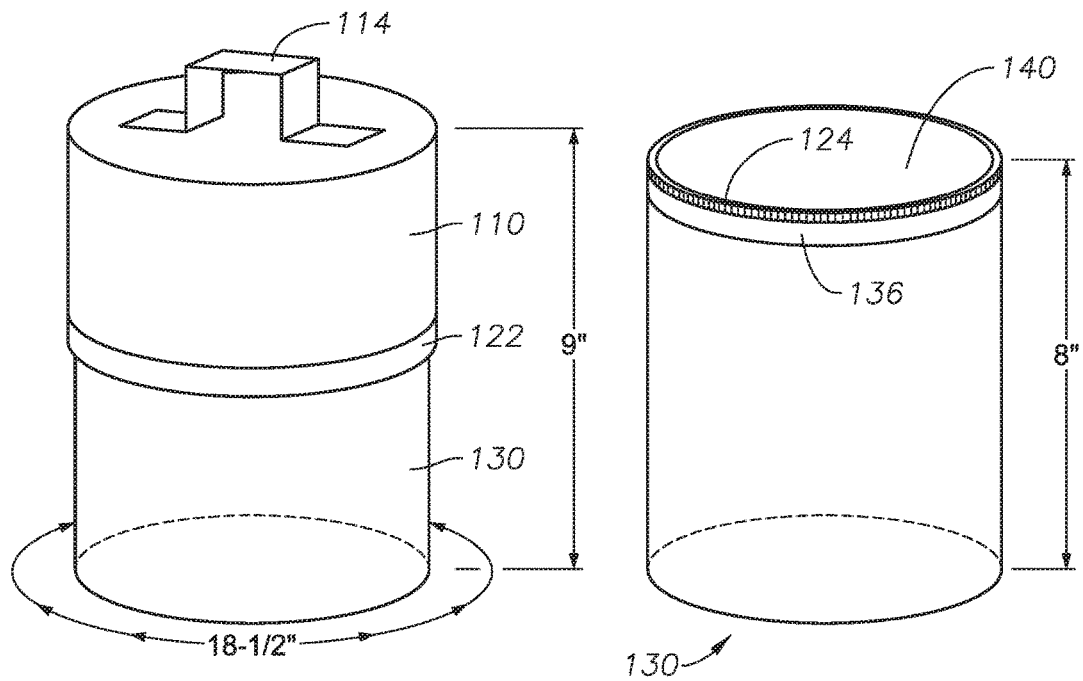
FIG. 3F is a view of the entire water-resistant VAD bag employing a HeartMate® device according to a dimensioned embodiment.

FIGS. 3A, 3B, 3C, 3D, 3E, and 3F are views of different aspects of the water-resistant VAD bag 100 employing a HeartMate® device according to an embodiment. FIG. 3A is a view of the entire water-resistant VAD bag 100 employing a HeartMate® device according to an embodiment. FIG. 3B is a view of the upper unit 110 of the water-resistant VAD bag 100 employing a HeartMate® device according to an embodiment. FIG. 3C is a view of the lower unit 130 of the water-resistant VAD bag 100 employing a HeartMate® device according to an embodiment. FIG. 3D is a view of the handle 114 attached to the water-resistant VAD bag 100 employing a HeartMate® device according to a dimensioned embodiment. FIG. 3E is a view of the upper unit 110 of the water-resistant VAD bag 100 employing a Heart-Mate® device according to a dimensioned embodiment.

As shown in FIG. 3E, in certain embodiments, a water-resistant VAD bag 100 employing a HeartMate® device has an upper unit 110 with a height of 4.5 inches and a diameter of 6 inches. As shown in FIG. 3F, in certain embodiments, a water-resistant VAD bag 100 employing a HeartMate® device has a lower unit 130 with a height of 8 inches, such the total height of the combination of the upper unit 110 and the lower unit 130 measures from the handle 114 to the bottom of the lower unit 130 is about 9 inches.

Figure 4A:
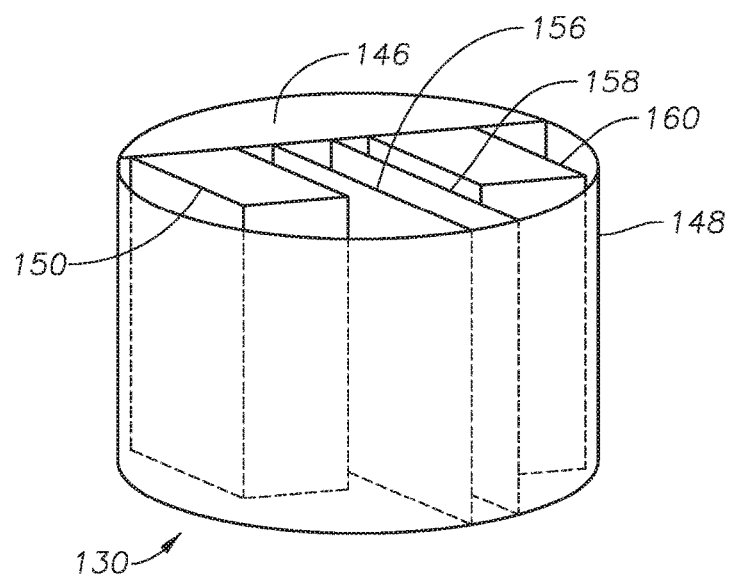
FIG. 4A is a partial cross-sectional view of the entire water-resistant VAD bag showing the controller compartment and the battery compartment according to an embodiment.

Shown in FIG. 4A is a partial cross-sectional view of the entire water-resistant VAD bag 100 showing the controller compartment 150 and the battery compartment 160 according to an embodiment of the present technology. As shown, the controller compartment 150 and the battery compartment 160 are separated by the first inserted sleeve 156 and the second inserted sleeve 158. The first inserted sleeve 156 and the second inserted sleeve 158, each of which may be of double thickness and double stitched, may function as dividers to separate the controller compartment 150 from the battery compartment 160. The inner sleeve 146 is insertable into the lower unit of the water-resistant VAD bag 100, has the shape of a circle, and covers the controller sleeve 154 and the battery sleeve 164. The inner layer 146 is insertable into the lower unit 130 of the water-resistant VAD bag 100 and positioned inside the lower unit 130.

Figure 4B:
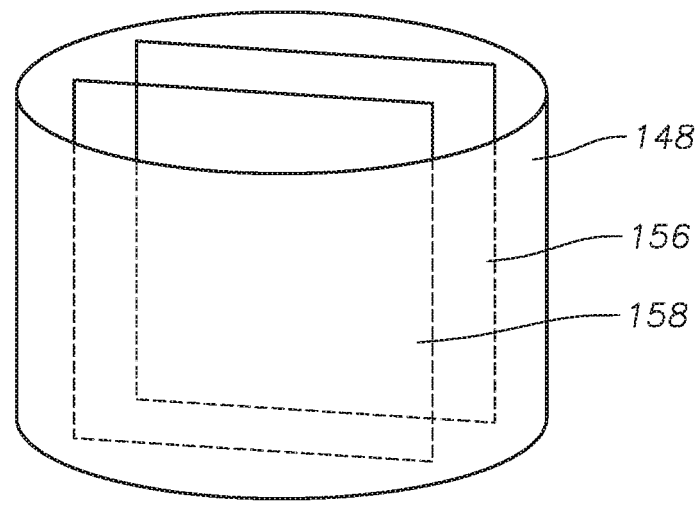
FIG. 4B is a view of the inserted sleeves and the inner layer according to an embodiment.

Shown in FIG. 4B is a view of the inserted sleeves (the first inserted sleeve 156 and the second inserted sleeve 158) and the inner layer 148 according to an embodiment of the present technology. Each of the first inserted sleeve 156 and the second inserted sleeve 158 and the inner layer 148 serve as a barrier to protect the controller compartment 150 and and the battery compartment 160 from any water, moisture, and debris that may have entered the water-resistant VAD bag 100 of the present technology.

Figure 4C:
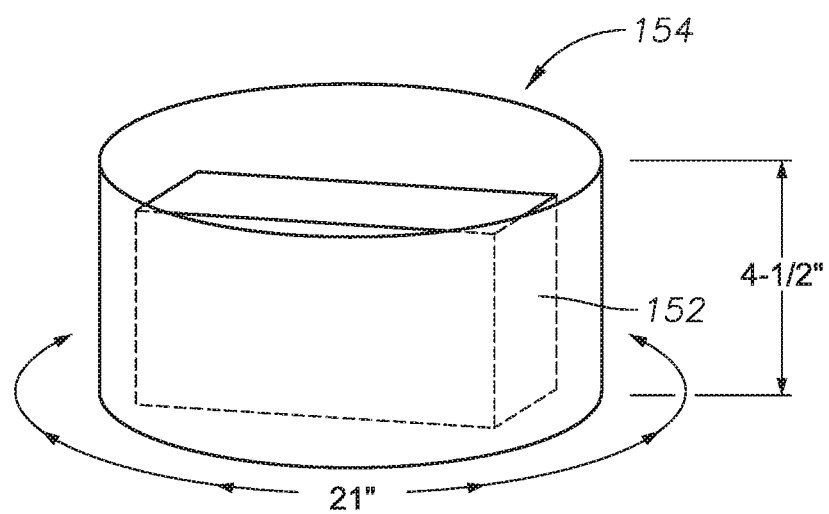
FIG. 4C is a view of the controller compartment according to a dimensioned embodiment.

FIG. 4C is a view of the controller compartment 150 according to an embodiment of the present technology. The controller compartment 150 contains the VAD controller 152, which may be a small computer that monitors the VAD pump 105, and the controller sleeve 154, which may be lining inside and flush to the wall of the controller compartment 150. Thus, for example, the controller compartment 150 may house a VAD controller 152 that may be sensitive to water damage. In some embodiments, the controller compartment 150 is about 4.5 inches in height and about 21 inches in circumference.

Figure 4D:
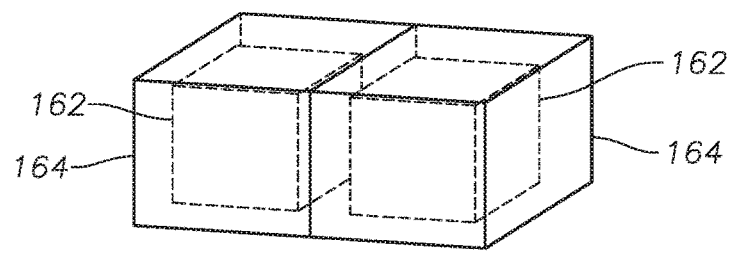
FIG. 4D is a view of the battery compartment according to a dimensioned embodiment.
Figure 4E:
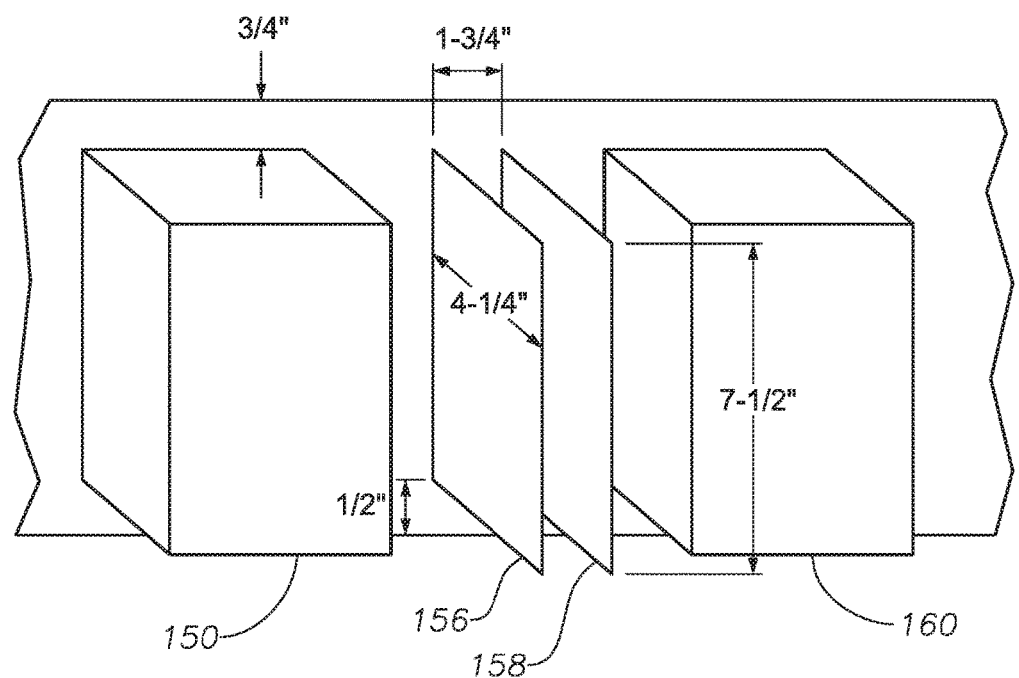
FIG. 4E is a view showing the controller compartment, inserted sleeves, and the battery compartment according to a dimensioned embodiment.

Shown in FIG. 4D is a view of the battery compartment 160 according to an embodiment of the present technology. The battery sleeve 164 is insertable into at least one battery compartment 160, which may house at least one VAD battery 162 that may be sensitive to water damage. The battery sleeve 164 may be lining inside and flush to the wall of the battery compartment 160 and may be configured to block entry of moisture into the battery compartment 160. The battery compartment 160 is substantially of cubic shape with dimensions of about 2.25 inches by about 4.25 inches by about 3.25 inches.

Shown in FIG. 4E is a view showing the controller compartment 150, inserted sleeves (the first inserted sleeve 156 and the second inserted sleeve 158), and the battery compartment 160 according to a dimensioned embodiment of the present technology. The first inserted sleeve 156 and the second inserted sleeve 158 are separated by a distance of about 1.75 inches. Each of the inserted sleeves (the first inserted sleeve 156 and the second inserted sleeve 158) is substantially a rectangle of about 4.25 inches by about 7.25 inches. Each of the inserted sleeves (the first inserted sleeve 156 and the second inserted sleeve 158) and the inner sleeve 146 is separated by a distance of about 0.75 inch.

In certain embodiments, the water-resistant VAD bag 100 of the present technology as shown in FIGS. 1, 2A, 2B, 2C, 2E, 2F, 2G, 3A, 3B, 3C, 3E, 3F, 4A, 4B, 4C, 4E, 4F may include internal walls, exterior walls, internal sleeves (such as inner sleeve 146, controller sleeve 154, first inserted sleeve 156, second inserted sleeve 158), and inner layer 148 that may be constructed with 1050 Denier Nylon Ballistic cloth coated condura fabric, which provides waterproof properties to water-resistant VAD bag 100. In certain embodiments, the construction of and the components of the water-resistant VAD bag 100 of the present technology may consist of styrene 0.030, polypropylene black pipping, waterproof lining, P2200 webbing with UV inhibitors, and foam ⅛" polyethylene. In some embodiments, the construction of and the components of the water-resistant VAD bag 100 of the present technology may be dust-free, non-abrasive, shock resistant, and moisture proof.

One of ordinary skill in the relevant art would have understood that the components of the water-resistant VAD bag 100 described above may be constructed of other materials that may provide the bag or pouch with similar characteristics (i.e., dust free, non-abrasive, shock resistant, moisture proof, water proof, etc.).

Although the technology herein has been described with reference to particular embodiments, it is to be understood that these embodiments are merely illustrative of the principles and applications of the present technology. It is therefore to be understood that numerous modifications can be made to the illustrative embodiments and that other arrangements can be devised without departing from the spirit and scope of the present technology as defined by the appended claims.

What is claimed is:

1. A water-resistant ventricular assist device (VAD) bag, comprising:
an upper unit of flexible nylon having the shape of a cylinder, the upper unit comprising a first elongated strap with a clip on a first end and second elongated strap on a second end without a clip, a cover on top of the upper unit with a handle sewn into the cover, and a zipper around a bottom of the cover;
a lower unit of flexible nylon having the shape of a cylinder, the lower unit comprising a connecting strap and a third elongated strap with a receptacle for the clip on the first elongated strap from the upper unit, the zipper on the top of the lower unit, wherein the connecting strap and second elongated strap are sewn into the lower unit and the upper unit; and
a controller sleeve that is insertable into the lower unit of the VAD bag, the controller sleeve comprising a controller compartment for housing a VAD controller sensitive to water damage;
a battery sleeve that is insertable into the lower unit of the VAD bag, the battery sleeve comprising at least one battery compartment for housing at least one VAD battery sensitive to water damage;
two inserted sleeves positioned in between the controller sleeve and the battery sleeve;
an inner sleeve that is insertable into the lower unit of the VAD bag, the inner sleeve having the shape of a circle and covering the controller sleeve and the battery sleeve; and
an inner layer that is insertable into the lower unit of the VAD bag, the inner layer positioned inside the lower unit.

2. The water-resistant VAD bag of claim 1, wherein the controller sleeve is configured to block entry of moisture into the controller compartment.

3. The water-resistant VAD bag of claim 1, wherein the battery sleeve is configured to block entry of moisture into the battery compartment.

4. The water-resistant VAD bag of claim 1, wherein the controller compartment is about 4.5 inches in height and about 21 inches in circumference.

5. The water-resistant VAD bag of claim 1, wherein the battery compartment is substantially of cubic shape with dimensions of about 2.25 inches by about 4.25 inches by about 3.25 inches.

6. The water-resistant VAD bag of claim 1, wherein the upper unit has a circumference of about 21.25 inches and the lower unit has a circumference of about 24.25 inches.

7. The water-resistant VAD bag of claim 1, wherein the upper unit has a height measured from the zipper to the handle of about 3.25 inches or about 4.25 inch or about 1 inch.

8. The water-resistant VAD bag of claim 1, wherein the total height of the combination of the upper unit and the lower unit measured from the handle to the bottom of the lower unit is about 6.75 inches or is about 9 inches.

9. The water-resistant VAD bag of claim 1, wherein a webbing circumscribes the upper unit and is about 1 inch thick.

10. The water-resistant VAD bag of claim 1, wherein the clip is about 0.75 inch long.

11. The water-resistant VAD bag of claim 1, wherein the top of the handle is a rectangle of about 4.25 inches by about 1.5 inches or a rectangle of about 3.75 inches by about 1.25 inches.

12. The water-resistant VAD bag of claim 1, wherein the connecting strap is about 4.25 inches long.

13. The water-resistant VAD bag of claim 1, wherein the two inserted sleeves are separated by a distance of about 1.75 inches.

14. The water-resistant VAD bag of claim 1, wherein the inserted sleeve is substantially a rectangle of about 4.25 inches by about 7.25 inches.

15. The water-resistant VAD bag of claim 1, wherein the inserted sleeve and inner sleeve are separated by a distance of about 0.75 inch.

16. A water-resistant ventricular assist device (VAD) system, comprising:
a water-resistant VAD bag, comprising:
an upper unit of flexible nylon having the shape of a cylinder, the upper unit comprising a first elongated strap with a clip on a first end and second elongated strap on a second end without a clip, a cover on top of the upper unit with a handle sewn into the cover, and a zipper around a bottom of the cover;
a lower unit of flexible nylon having the shape of a cylinder, the lower unit comprising a connecting strap and a third elongated strap with a receptacle for the clip on the first elongated strap from the upper unit, the zipper on the top of the lower unit, and wherein the connecting strap and second elongated strap are sewn into the lower unit and the upper unit; and a controller sleeve that is insertable into the lower unit of the VAD bag, the controller sleeve comprising a controller compartment for housing a VAD controller sensitive to water damage; and a battery sleeve that is insertable into the lower unit of the VAD bag, the battery sleeve comprising at least one battery compartment for housing at least one VAD battery sensitive to water damage;

two inserted sleeves positioned in between the controller sleeve and the battery sleeve;

an inner sleeve that is insertable into the lower unit of the VAD bag, the inner sleeve having the shape of a circle and covering the controller sleeve and the battery sleeve; and an inner layer that in insertable into the lower unit of the VAD bag, the inner layer positioned inside the lower unit;

a water-resistant percutaneous lead configured to electrically couple the VAD controller to a VAD pump and to regulate VAD pump function; and an AC adapter for electrically coupling the VAD controller to an electrical outlet.

17. The water-resistant VAD system of claim 16, further comprising:
a power module configured to provide continuous power to the VAD system.

18. The water-resistant VAD system of claim 16, further comprising:
a battery charger configured to provide external battery power to the VAD controller.

19. The water-resistant VAD system of claim 16, further comprising:
an external display device configured to present performance of the VAD system and to provide touch input to controller operating parameters.

20. A method of making a water-resistant VAD bag sensitive to water damage, the method comprising:
providing an upper unit of flexible nylon having the shape of a cylinder, the upper unit comprising a first elongated strap with a clip on a first end and second elongated strap on a second end without a clip, a cover on top of the upper unit with a handle sewn into the cover, and a zipper around a bottom of the cover;

providing a lower unit of flexible nylon having the shape of a cylinder, the lower unit comprising a connecting strap and a third elongated strap with a receptacle for the clip on the first elongated strap from the upper unit, the zipper on the top of the lower unit, wherein the connecting strap and second elongated strap are sewn into the lower unit and the upper unit, the lower unit comprising:

a controller sleeve that is insertable into the lower unit of the water-resistant VAD bag, the controller sleeve comprising a controller compartment for housing a VAD controller sensitive to water damage;

a battery sleeve that is insertable into the lower unit of the water-resistant VAD bag, the battery sleeve comprising at least one battery compartment for housing at least one VAD battery sensitive to water damage;

two inserted sleeve positioned in between the controller sleeve and the battery sleeve;

an inner sleeve that is insertable into the lower unit of the water-resistant VAD bag, the inner sleeve having the shape of a circle and covering the controller sleeve and the battery sleeve; and an inner layer that in insertable into the lower unit of the water-resistant VAD bag, the inner layer positioned inside the lower unit;

positioning at least one inserted sleeve in between the controller sleeve and the battery sleeve;

placing the inner sleeve into the lower unit of the water-resistant VAD bag to cover the controller sleeve and the battery sleeve;

placing the inner layer into the lower unit of the water-resistant VAD bag to cover the lower unit;

sealing the upper unit with the lower unit by zipping the zipper around a bottom of the upper unit and the on the top of the lower unit; and clipping the upper unit with the lower unit by engaging the clip on a first end with the receptacle for the clip on the third elongated strap.

* * * * *